United States Patent [19]

Burk et al.

[11] 4,049,696

[45] Sept. 20, 1977

[54] 3-((4-(2,2-DICHLORO-1,1-DIFLUOROETHOXY)PHENYL)SULFONYL)-2-PROPENENITRILE

[75] Inventors: George A. Burk, Bay City; Christian T. Goralski; Craig E. Mixan, both of Midland, all of Mich.

[73] Assignee: The Dow Chemical Company, Midland, Mich.

[21] Appl. No.: 758,281

[22] Filed: Jan. 10, 1977

[51] Int. Cl.$^2$ ............................................ C07C 121/75
[52] U.S. Cl. .................................. 260/465 F; 424/304
[58] Field of Search ........................................ 260/465 F

[56] References Cited

U.S. PATENT DOCUMENTS

| 3,159,532 | 12/1964 | Heininger et al. | 424/304 |
|---|---|---|---|
| 3,541,119 | 11/1970 | Richter et al. | 260/397.6 |
| 3,821,399 | 6/1974 | Richter | 424/304 |

*Primary Examiner*—Dolph H. Torrence
*Attorney, Agent, or Firm*—Theodore Post; C. Kenneth Bjork

[57] ABSTRACT

3-((4-(2,2-Dichloro-1,1-difluoroethoxy)phenyl)sulfonyl)-2-propenenitrile is prepared by mixing together 2-chloro-3-((4-(2,2-dichloro-1,1-difluoroethoxy)-phenyl)sulfonyl)propanenitrile and a slight molar excess of triethylamine in the presence of benzene as reaction medium.

1 Claim, No Drawings

3-((4-(2,2-DICHLORO-1,1-DIFLUOROETHOXY)-PHENYL)SULFONYL)-2-PROPENENITRILE

DESCRIPTION OF CLOSEST PRIOR ART KNOWN

S. A. Heininger et al., in U.S. Pat. No. 3,159,532, patented December 1, 1964, disclose certain arylsulfonyl alkenenitriles, which are said to inhibit the growth of bacteria and fungi. Among these are 3-(4-bromophenyl-sulfonyl) acrylonitrile and other halo and polyhalo analogs thereof. S. U. K. A. Richter et al., in U.S. Pat. No. 3,541,119, patented November 17, 1970, disclose compounds of the type benzenesulfonylacrylonitrile wherein the benzene moiety may have lower alkyl or p-acetamido substitution. The compounds are said to have antimicrobial utility. S. U. K. A. Richter, in U.S. Pat. No. 3,821,399, discloses antimicrobial compounds of the type phenylsulfonylacrylonitrile wherein the phenyl moiety may have lower alkyl, acetamido or amino substitution.

SUMMARY OF THE INVENTION

This invention concerns the compound 3-((4-(2,2-dichloro-1,1-difluoroethoxy)phenyl)sulfonyl)-2-propene-nitrile. The compound has antimicrobial utility.

The compound is prepared by mixing together 2-chloro-3-((4-(2,2-dichloro-1,1-difluoroethoxy)phenyl)-sulfonyl)propanenitrile and a slight molar excess of triethylamine in the presence of benzene as reaction medium. The reaction which takes place is represented by the following schematic equation

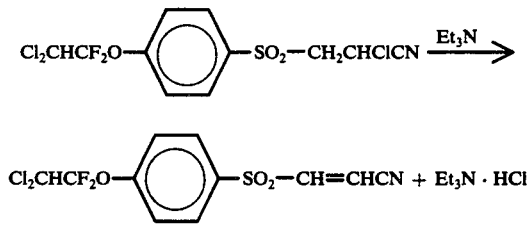

The reaction mixture is filtered to remove the by-product triethylamine hydrochloride. The benzene is removed in vacuo from the filtrate and the residue which remains is crystallized from methanol/water to give the title compound as a tan solid, melting at 89°–90° C.

The compound has antimicrobial utility. When evaluated in the conventional in vitro agar Petri dish dilution test for determining antimicrobial activity, 100% growth inhibition against the following organisms was observed at the indicated parts per million.

| 3-((4-(2,2-DICHLORO-1,1-DIFLUOROETHOXY)-PHENYL)SULFONYL-2-PROPENENITRILE MIC, PPM | |
|---|---|
| P. aeruginosa | 100.00 |
| S. aureus | 5.00 |
| C. albicans | 50.00 |
| T. mentagrophytes | 10.00 |
| K. pneumoniae M-1 Midland Hospital | 100.00 |
| P. chrysogenum | 10.00 |
| A. niger | 10.00 |
| B. subtilis | 1.00 |
| C. pelliculosa | 10.00 |
| P. pullulans | 50.00 |
| C. ips | 50.00 |
| Trichoderm Sp. Madison P-42 | 100.00 |
| S. marcescens NIH | 50.00 |
| Torulopsis Species | 50.00 |
| A. fumigatus | 50.00 |
| C. albicans NIH | 50.00 |
| E. coli ATCC 11229 | 50.00 |

The following additional description and example further describe the invention and the manner and process of making it to enable the art skilled to make and use the same and set forth the best mode contemplated by the inventors of carrying out the invention.

EXAMPLE 3-((4-(2,2-Dichloro-1,1-difluoroethoxy)phenyl)-sulfonyl-2-propenenitrile To 3.0 g (0.079 mol) of 2-chloro-3-((4-(2,2-dichloro-1,1-difluoroethoxy)phenyl)sulfonyl)propanenitrile in 100 ml of benzene was added a slight molar excess of triethylamine. The reaction mixture was filtered to remove the triethylamine hydrochloride produced. The benzene was removed in vacuo from the filtrate, and the residue which remained was crystallized from methanol/ water to give 1.5 g of the title compound as a tan solid, mp 89°–90° C.

Anal. Calcd. for $C_{11}H_7Cl_2F_2NO_3S$: C, 38.5; H, 2.05; Cl, 20.7; N, 4.10. Found: C, 38.65; H, 2.23; Cl, 20.7; N, 4.23.

PREPARATION OF THE STARTING MATERIAL

The preparation of the starting material, 2-chloro-3-((4-(2,2-dichloro-1,1-difluoroethoxy)phenyl)sulfonyl)-propanenitrile and the starting material for it are disclosed in our co-pending patent application, Ser. No. 758,284, entitled "2-Chloro-3-((4-(2,2-dichloro-1,1-difluoroethoxy)phenyl)sulfonyl)propanenitrile," filed Jan. 10, 1977.

What is claimed is:

1. The compound 3-((4-(2,2-dichloro-1,1-difluoroethoxy)phenyl)sulfonyl-2-propenenitrile.

* * * * *